United States Patent
Perren et al.

(10) Patent No.: US 11,986,572 B2
(45) Date of Patent: May 21, 2024

(54) DEVICE FOR THE NON-INVASIVE INDUCTION OF DYNAMIC DEFORMATION OF BODY TISSUE TO DIFFERENTIATE TISSUE CELLS

(71) Applicants: Nicolas Perren, Dessau (DE); Alice Perren, Davos (CH)

(72) Inventors: Nicolas Perren, Dessau (DE); Stephan Perren, Davos (CH)

(73) Assignee: Nicolas Perren, Dessau (DE)

( * ) Notice: Subject to any disclaimer, the term of this patent is extended or adjusted under 35 U.S.C. 154(b) by 421 days.

(21) Appl. No.: 16/754,434

(22) PCT Filed: Oct. 17, 2017

(86) PCT No.: PCT/CH2017/000093
§ 371 (c)(1),
(2) Date: Apr. 8, 2020

(87) PCT Pub. No.: WO2019/075584
PCT Pub. Date: Apr. 5, 2019

(65) Prior Publication Data
US 2021/0196857 A1    Jul. 1, 2021

(51) Int. Cl.
| | | |
|---|---|---|
| *A61L 27/36* | (2006.01) | |
| *A61L 27/04* | (2006.01) | |
| *A61L 27/06* | (2006.01) | |
| *A61L 27/08* | (2006.01) | |
| *A61L 27/38* | (2006.01) | |

(52) U.S. Cl.
CPC .......... *A61L 27/365* (2013.01); *A61L 27/042* (2013.01); *A61L 27/045* (2013.01); *A61L 27/06* (2013.01); *A61L 27/08* (2013.01); *A61L 27/3608* (2013.01); *A61L 27/3691* (2013.01); *A61L 27/3821* (2013.01); *A61L 27/3847* (2013.01); *A61L 2430/02* (2013.01)

(58) Field of Classification Search
None
See application file for complete search history.

(56) References Cited

U.S. PATENT DOCUMENTS

| | | | |
|---|---|---|---|
| 4,323,056 A | 4/1982 | Borrelli et al. | |
| 2010/0049330 A1 | 2/2010 | Horvath | |
| 2014/0005794 A1* | 1/2014 | Horvath | A61F 2/28 623/23.5 |

FOREIGN PATENT DOCUMENTS

| | | |
|---|---|---|
| DE | 19600744 A1 | 7/1997 |
| DE | 102006047248 A1 | 4/2008 |
| DE | 102011014789 A1 | 9/2012 |
| EP | 1060731 A1 | 12/2000 |
| WO | 2008043484 A2 | 4/2008 |
| WO | 2012123095 A1 | 9/2012 |

OTHER PUBLICATIONS

Liu, T.-Y., et al., Adv. Funct. Mater. 19: 616-623 (2009). (Year: 2009).*
Asanami, S. and K. Shimono, Mutation Research 390: 79-83 (1997). (Year: 1997).*
Ortega, D. and Q. Pankhurst, Nanoscience 1: 60-88 (2013). (Year: 2013).*
International Search Report dated Jun. 15, 2018 filed in PCT/CH2017/000093.

* cited by examiner

*Primary Examiner* — David J Blanchard
*Assistant Examiner* — Daniel F Coughlin
(74) *Attorney, Agent, or Firm* — Rankin, Hill & Clark LLP

(57) ABSTRACT

The device is intended for the noninvasive induction of dynamic deformation of body tissue to differentiate tissue cells. It comprises the following components: (i) a suspension of particles suspended in solution; and (ii) an external actuator which is capable of magnetically, electrically, vibrationally, or thermally stimulating the suspended particles.

14 Claims, 8 Drawing Sheets

Figure 1A:
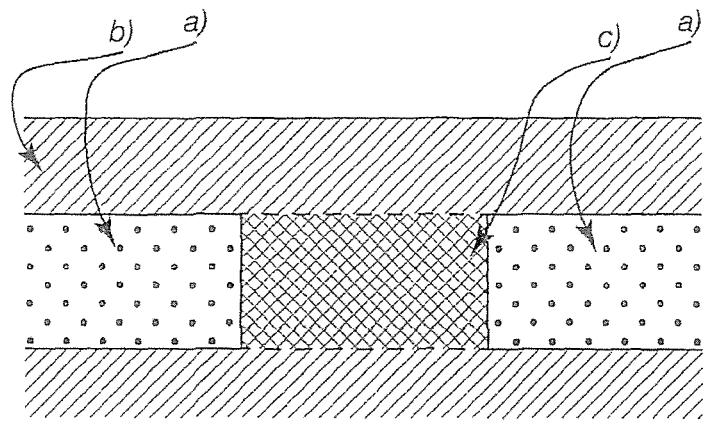

DEVICE FOR THE NON-INVASIVE INDUCTION OF DYNAMIC DEFORMATION OF BODY TISSUE TO DIFFERENTIATE TISSUE CELLS

The invention relates to a device for generating body tissue deformation according to the preamble of claim 1 and a method according to the preamble of claim 26.

It is known that reparative body cells reform under deformation into various types of tissue, for example, bone. The bone supports the elements of the locomotor system and thus enables its function. When broken by overload, the bone loses its mechanical function. The repair of the function of the broken bone, bone fracture healing, requires a solid bridging of the bone in the anatomically correct location. Successful bone fracture healing has to be induced, enabled, and maintained. The mechanical conditions play a decisive role in this case. This applies not only to the bone fracture healing but rather also to tissue healing in general and also to the production of tissue inside or outside bodies of human and animal (for example, tissue engineering).

Various known medical treatment methods are based on the application of the findings of this strain theory. Thus, for example, callous strain by the Illizarov apparatus, implantable mechatronic controlled intramedullary nails, and other similar methods have been used for years for bone lengthening or defect bridging. These methods all have the disadvantage that they necessitate long-lasting processes, which are painful to the patient, and require multiple operations. The advantage of a single injectable method is in the increased level of acceptance by the patient, since the method is carried out very gently and is borne easily.

An injectable method for callous strain is known from WO 2012123095. This known device relates to a granulate mixture for regeneration of a bone by means of three-dimensional strain for callous strain. The granulate mixture contains rigid and deformable granulate which, after the injection into the bone defect, executes a strain on the surrounding body tissue by way of the expansion of a hydrogel in the deformable granulate. This known device has the disadvantage that the movement is nonrecurring and irreversible due to the use of an osmotically acting method, for example, by application of hydrogel. After reaching the final extension, no further movement is executed. The activation of the tissue differentiation requires a repeated movement, however. It is also disadvantageous that the spectrum of the amplitude and speed of the movement is greatly restricted by the chemical properties of the hydrogel. The stimulation of the bone formation is thus not reliable and is short-term and has a significantly lesser result than in the present invention. A further disadvantage is that after introduction of the granulate mixture into the body, the nonrecurring movement can no longer be changed. It is thus not possible to react to changed conditions which occur during the treatment, which is important to adapt the tissue formation in the course of the healing process optimally to the different consecutive stages of the fracture healing, which requires different values of the strain required to induce the differentiation.

Furthermore, a framework for artificial three-dimensional callous distraction of a bone is known from WO 2008/043484, which can be introduced into the body of a patient. An externally attached apparatus can move the framework from the outside, which in turn can deliver its movement to the surrounding body cells of the patient. The disadvantages of this known device are as follows:

(i) the framework comprises a complicated fiber composite having intermediate spaces to be able to effectuate forces on the surrounding tissue of the patient by a strain/shrinkage of the framework;
(ii) if multiple frameworks are used, the individual framework is only activated by a volume change, but the relative location of the individual frameworks in relation to one another is not.

The present invention wishes to provide a remedy here. The invention is based on the object of providing a device which permits optimum and targeted dynamic deformation of body tissue on the basis of its simple and safe handling.

The following definitions are used in conjunction with the invention:

Strain (symbol $\varepsilon$):

Strain is understood hereafter as a specification of the relative deformation (lengthening or shortening) in various directions of a body under load, for example, due to force action. If the dimension of the body increases, this is referred to as positive strain, otherwise as negative strain or compression.

The critical element of the mechanism in relation to bone healing is tissue deformation (strain $\varepsilon$ in the meaning of lengthening and shortening, in various directions). On the one hand, the healing is stimulated if the tissue strain is greater than the minimum amount. The healing process is not triggered if there is insufficient strain. On the other hand, the bridging of the fracture is only possible if the present strain of the tissue element is not greater than the fracture elongation of the repairing tissue. There is a bandwidth of strain, which is the condition for swift and reliable healing, between these two conditions, induction and tolerance. The healing is disturbed if the inter-fragmentary strain is outside the mentioned bandwidth. Healing delays or pseudoarthroses result. The treatment of such healing disorders requires a correction of the tissue strain. The strain can be returned into the mentioned bandwidth by enlargement or reduction in size and the healing can thus be enabled.

Strain Frequency:

The frequency of the tissue deformation per unit of time, the term strain (strain=dL/L) is independent of direction here (but is often used as contrary to compression).

Noninvasive Induction of Dynamic Deformation of Body Tissue:

Noninvasive=without tissue traumatization, dynamic deformation=time-dependent deformation of body tissue. In conjunction with the invention, this combination is supposed to describe an apparatus which, when externally attached without exogenous physical connection, exerts influence on the particles through the body tissue. No injury to the skin and tissue layers is thus caused. This is in contrast to the known Illizarov apparatus.

Heterotopic Tissue Formation:

Formation of tissue at locations where this tissue does not occur according to nature.

The advantages achieved by the invention in relation to the prior art can essentially be considered that:
the injection of a suspension of particles—activatable by means of the external actuator—suspended in solution permits extremely simple and accurate application;
repeated strain is exerted on the surrounding tissue by the externally induced movement of the particles, whereby the healing is optimized;
the externally activated movement can be controlled in intensity and frequency, whereby the strain can always be kept in the optimum range of the consecutive differentiation stages;

an excessively small or large strain which interferes with healing can be avoided;

the strain may be adapted optimally to the biological requirements and it is possible at any time to adapt the strain to the healing progress;

the present invention enables the tissue strain required for bone and tissue formation in optimum bandwidth of amplitude and frequency to be activated externally, i.e., without transcutaneous implant connection—which would promote infection;

the particles can be resorbed or intercalated harmlessly into body tissue by the body in the course of the healing process;

the invention can be applied anywhere tissue differentiation has to be stimulated or enabled by correction or generation of the optimum strain. Inter alia, for example, the generation of soft tissue or bone for therapeutic or aesthetic applications is possible. In the case of bone lengthening according to the Illizarov method, presently lengthening is performed in multiple stages in daily steps of millimeters, since insufficient strain would result after larger steps, which does not cause reliable bone formation. By application of the device according to the invention, the optimum strain for bone formation is achieved even with lengthening steps in centimeters. The time for wearing the external fixators, which annoy the patient, can be substantially shortened or avoided by large individual steps of the strain.

In the case of surgical interventions which require a transplantation of autologous (endogenous) bone, the required bone removal, for example, on the pelvis, causes long-lasting annoying pain. The device according to the invention can be used in patients to generate bone formation without the mentioned painful consequences of the bone removal.

The invention permits a reliable and painless strain, which is optimum for the tissue differentiation, to be generated in tissue, whereby a significant acceleration and high reliability is achievable in relation to the presently typical method.

The device according to the invention can be used to promote the healing at defined points. However, it can also be used to produce specific tissues in the body, which are used in general for "tissue engineering".

The device according to the invention can also be used for bone lengthening. It permits such extensions up to multiple centimeters in a single step with obtained induction of the tissue formation. This is the significant advantage over the known Illizarov method, which only permits daily extension steps in millimeters. The bone lengthening can thus be achieved in one or a few steps using the device according to the invention. The patient is completely functional again shortly after the operation and the weeks-long wearing of movement-obstructing external fixators structures can be made superfluous by the device according to the invention.

The device according to the invention can be used in all body parts.

Further advantageous designs of the invention can be commented on as follows:

In one particular embodiment of the invention, the particles can comprise body cells. In a further embodiment, the particles are nonporous.

The particles can be metallic, magnetic, magnetizable, electrically chargeable, massive, or thermally reactive. The particles preferably comprise one or more of the following substances:

platinum, titanium, steel, carbon steel, crystalline alloys based on iron, nickel, cobalt, amorphous or nano-crystalline alloys based on iron, nickel, cobalt; soft ferrites, cobalt samarium, neodymium iron-boron, AlNiCo, hard ferrites, martensitic steels, memory alloys.

The particles can also comprise electrically conductive materials, which have a resting potential different from the surroundings due to the insulating outer skin.

In a further embodiment, the particles comprise a bioresorbable material.

In a further embodiment, the particles are constructed homogeneously at least in the core thereof.

The particles can also be provided with a biocompatible outer skin, which is capable of promoting the growth of body cells.

The average diameter of the individual particles is expediently greater than 1 nm, preferably greater than 5 µm. The average diameter of the individual particles is expediently less than 5 mm, preferably less than 50 µm.

The average volume of the individual particles is expediently greater than 125 µm$^3$, preferably greater than 1000 µm$^3$. The average volume of the individual particles is expediently less than 100 mm$^3$, preferably less than 1 mm$^3$.

In a further embodiment, the particles do not have a fibrous structure.

The body-compatible liquid can contain bone-forming substances and/or tissue components and/or stem cells.

In one particular embodiment, at most $10^6$ particles, preferably at most $10^5$ particles are contained per mm$^3$ of body-compatible liquid.

The ratio between the total volume $\Sigma \text{Vol}_P$ of the particles and the volume of the liquid $\text{Vol}_F$ is expediently at most 10:1, preferably at most 2:1. The ratio between the total volume $\Sigma \text{Vol}_P$ of the particles and the volume of the liquid $\text{Vol}_F$ is expediently at least 1:1000, preferably at least 1:10.

In one special embodiment of the invention, the suspended particles comprise two or more different types, which are embodied so that, when stimulated by the actuator, a movement is executed between the different types of particles. This causes strain and compression of the cells or tissue surrounding them. This activation can be executed magnetically, electrically, by nanotechnology or quantum technology, based on mass inertia, thermally, or in another externally applied, tissue-penetrating, noninvasive manner.

The particles are preferably biocompatible and/or bioresorbable. The particles can also be enriched with calcium phosphate.

In one particular embodiment, the actuator can emit electromagnetic waves.

The actuator can comprise two magnetic coils, which alternately conduct current and can thus move magnetizable particles.

The actuator can also comprise a vibration source, which preferably emits in a frequency range of $1/10$-$1/1800$ Hz (s$^{-1}$).

The invention also comprises a method for noninvasive induction of dynamic deformation of body tissue for differentiating tissue cells, which is characterized by the following steps:

a) injecting a body-compatible liquid, in which volume-constant particles are suspended, into the body tissue to be deformed;

b) activating the particles by means of an external actuator without mechanical connection between actuator and particle, wherein
c) the activation is performed magnetically, electrically, vibrationally, or thermally; so that
d) a movement of the particles is generated, which results in deformations in the body tissue which stimulate the reparative differentiation of body cells.

In this method, the suspension of the particles diffuses into the body tissue to be treated, wherein the latter is deformed by the external activation. This is performed either by direct force transmission, if the body cells have grown on the particles, or via a displacement of the body cells.

In one particular embodiment, the body-compatible liquid can contain, in addition to the particles, body cells which are deformed by the external activation of the particles.

In a further embodiment, the particles are uniformly aligned by means of the external activation. In another embodiment, the particles execute a translation movement by means of the external activation.

The method can also enable a heterotopic tissue formation.

In one particular embodiment the actuator is actuated for at least one hour, preferably at least 3 hours. The actuator is expediently actuated for at most 6 months, preferably at most 1 month.

The alignment or shape change of the particles is expediently performed at least every 2 hours, preferably at least every 15 minutes. In another embodiment, the alignment or shape change of the particles is performed at most every second, preferably at most every 10 seconds.

The invention and refinement of the invention are explained in greater detail hereafter on the basis of the partially schematic illustrations of multiple exemplary embodiments.

The figures show:

An example of a surgical osteosynthesis by means of an implant which corresponds to the prior art and the device for noninvasive induction of dynamic deformation of body tissue.

FIG. 1a: The bone (a) in the body (b) is broken, the size of the defect (c) prevents, in the case of an operation by means of implants which correspond to the prior art, the healing of the bone due to a lack of bony bridging.

Figure 1B:
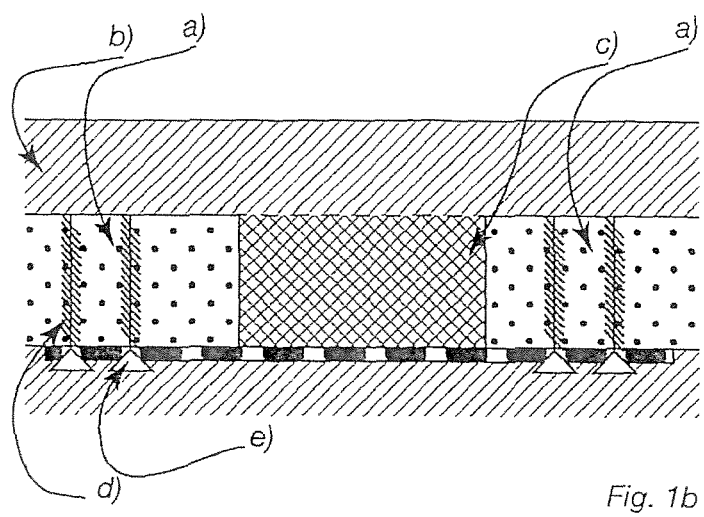

FIG. 1b: The bone fragments are connected in a frictionally-locked manner with or without screws (d) by means of an implant (e), which corresponds to the prior art, in such a way that little to no movement results between the bone fragments (a).

Figure 1C:
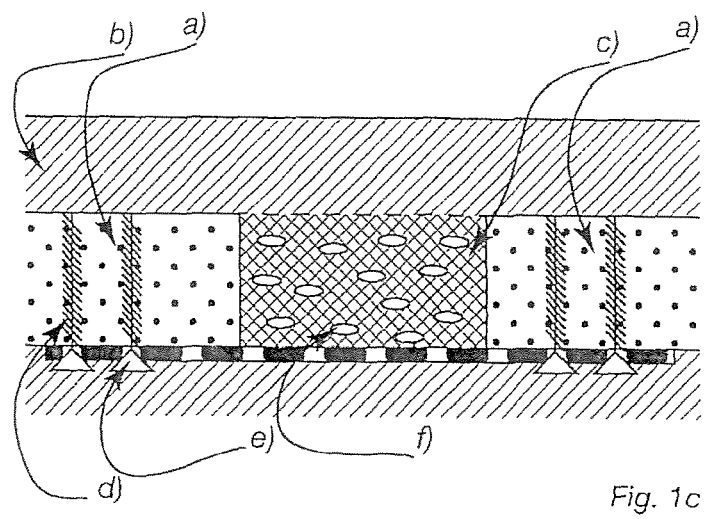

FIG. 1c: The solution of suspended particles (f) which can contain body cells is introduced into the defect. This can be performed, for example, by injection.

Figure 1D:
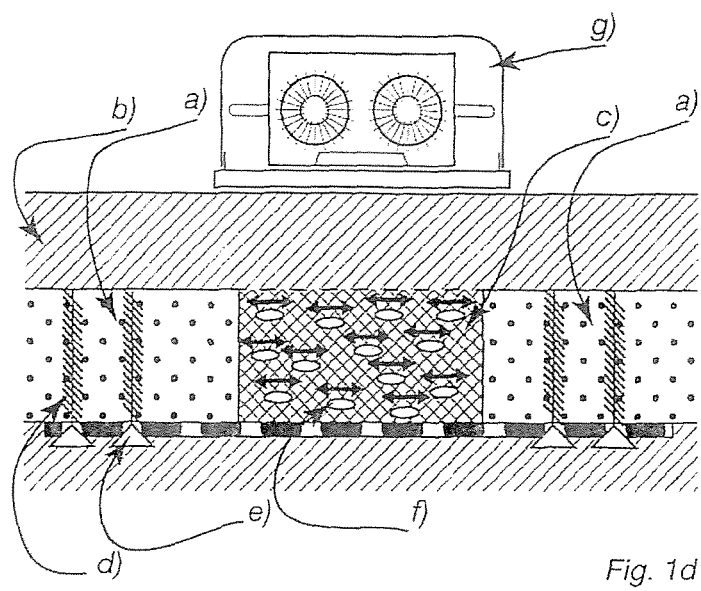

FIG. 1d: The actuator (g) is externally attached. Upon its activation, mutual movements and thus strain, which are transmitted to the body cells and/or the body tissue, result in the solution of suspended particles which can contain the body cells. The body cells and/or the body tissue begin to differentiate. In the present case, bone tissue forms in various differentiation stages. One important advantage of the present invention is that the induction can be adapted optimally to the individual progressing healing process.

Figure 1E:
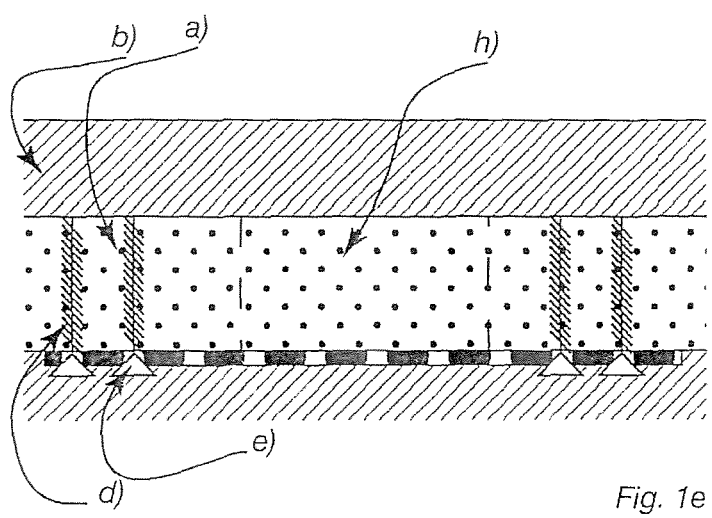

FIG. 1e: The bone has connected the two bone fragments again via a bone bridge (h).

An example of a bone lengthening by severing and surgical osteosynthesis by means of an implant which corresponds to the prior art and the device for noninvasive induction of dynamic deformation of body tissue.

Figure 2A:
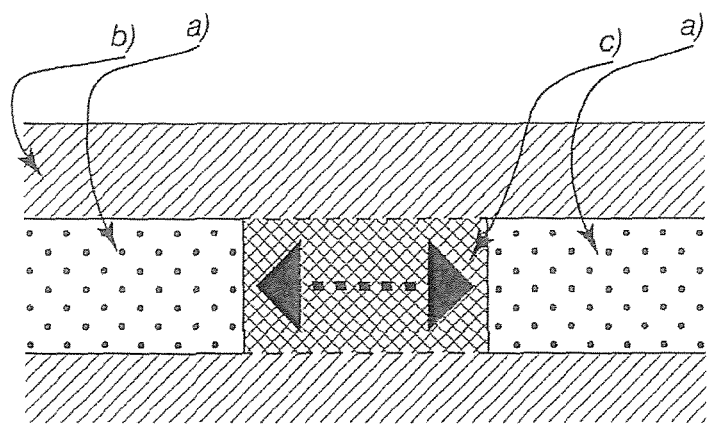

FIG. 2a: The bone (a) in the body (b) is surgically severed. The two bone fragments are pulled apart and fixed in the desired position by an implant which corresponds to the prior art. The size of the defect (c) prevents the healing of the bone due to a lack of bony bridging in the case of a one-step operation.

Figure 2B:
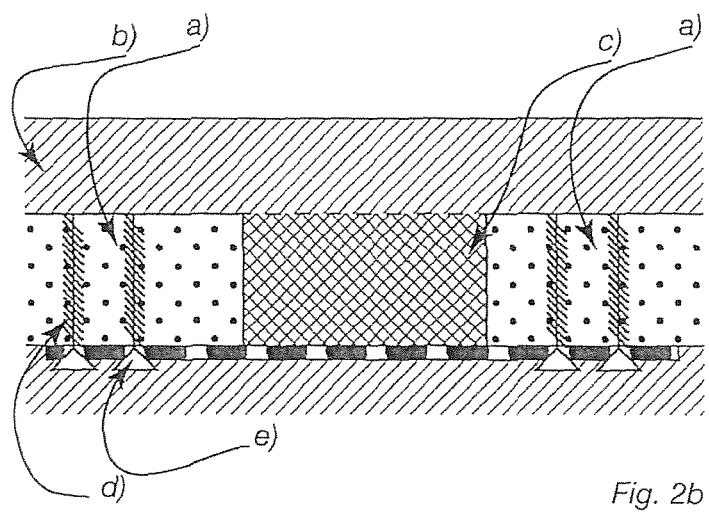

FIG. 2b: The bone fragments are connected in a frictionally-locked manner with or without screws (d) by means of an implant, which corresponds to the prior art, in such a way that little to no movement results between the bone fragments.

Figure 2C:
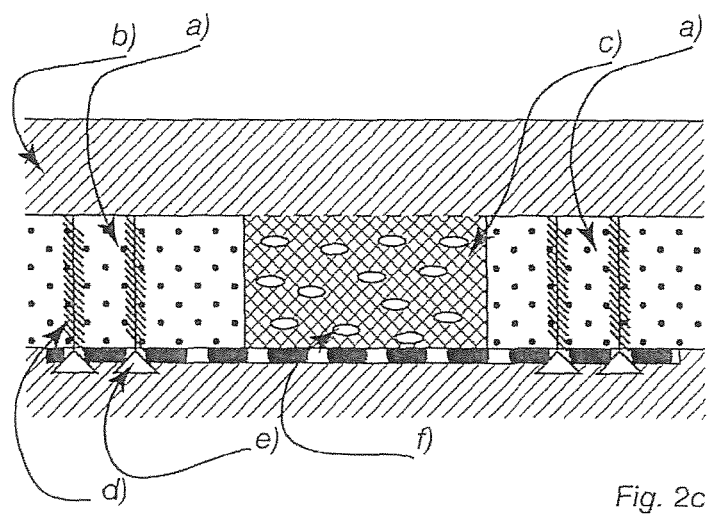

FIG. 2c: The solution of suspended particles which can contain body cells is introduced into the defect. This can be performed, for example, by injection.

Figure 2D:
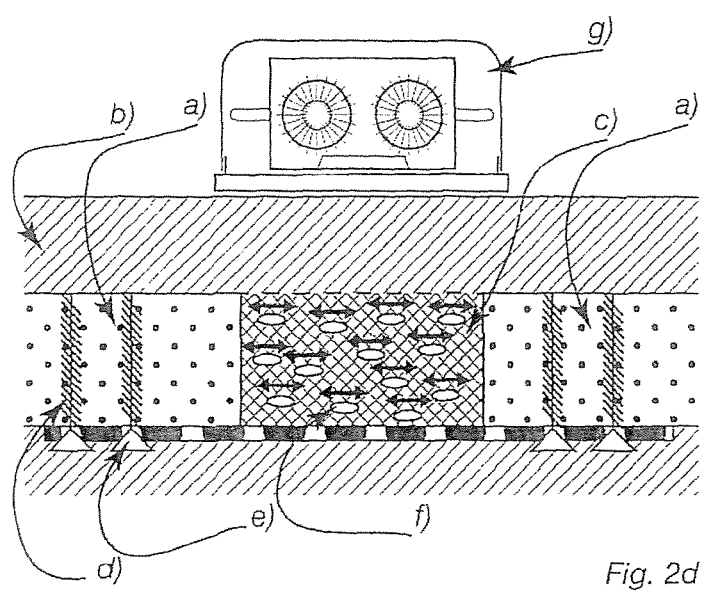

FIG. 2d: The actuator (g) is externally attached. Upon its activation, mutual movements and thus strain, which are transmitted to the body cells and/or the body tissue, result in the solution of suspended particles which can contain the body cells. The body cells and/or the body tissue begin to differentiate. In the present case, bone tissue forms in various differentiation stages. One important advantage of the present invention is that the induction can be adapted optimally to the individual progressing healing process.

Figure 2E:
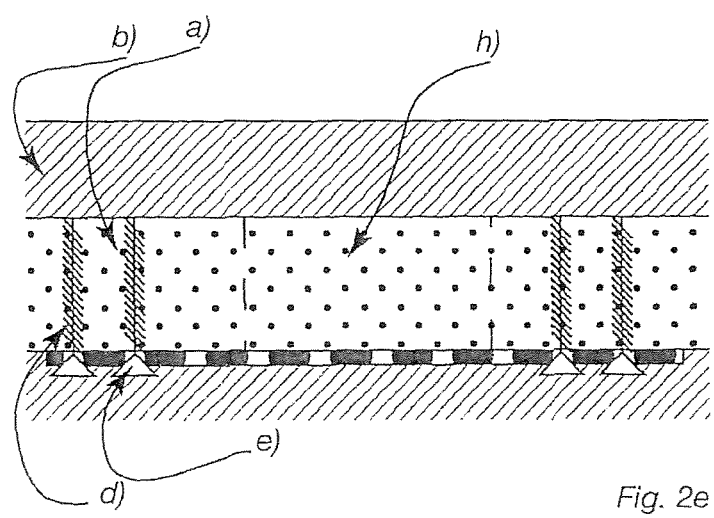

FIG. 2e: The bone has connected the two bone fragments again via a bone bridge (h). The bone has been expanded by the width of the introduced defect. A bone lengthening of up to 50 mm can thus take place in one step.

An example of tissue regeneration due to induced differentiation in patients by the device for noninvasive induction of dynamic deformation of body tissue.

Figure 3A:
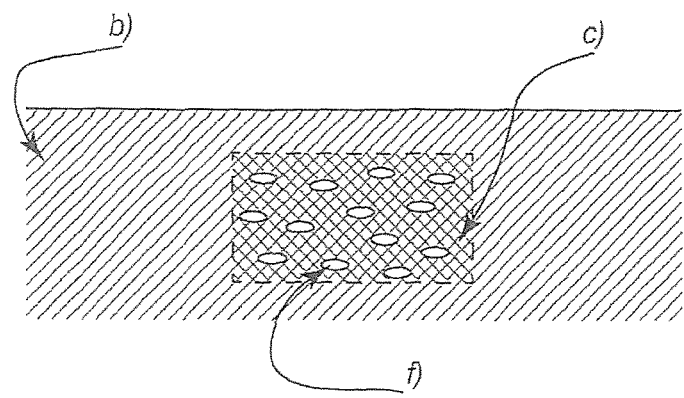

FIG. 3a: The solution of suspended particles which can contain body cells is introduced into muscle tissue of the patient. This can be performed, for example, by injection.

Figure 3B:
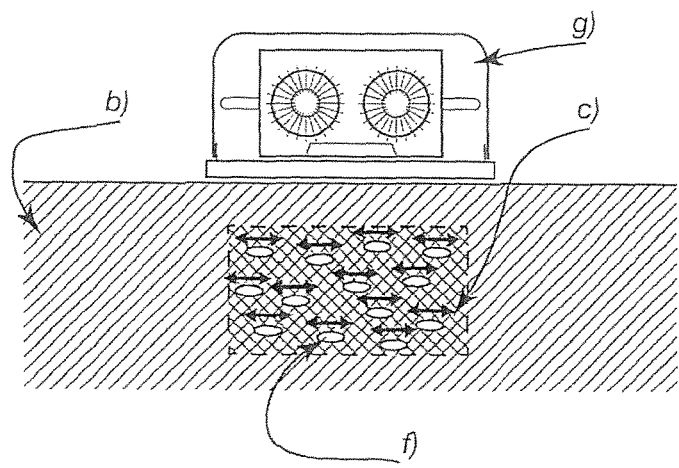

FIG. 3b: The actuator is externally attached. Upon its activation, mutual movements and thus strain, which are transmitted to the body cells and/or the body tissue, result in the solution of suspended particles which can contain the body cells. The body cells and/or the body tissue begin to differentiate.

Figure 3C:
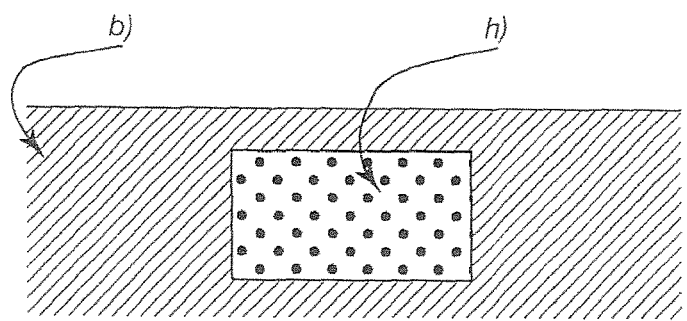

FIG. 3c: Different tissue is formed depending on the duration and strength, thus, for example, connective tissue, cartilage, or bone.

An example of bone restoration in the case of bone defect, for example, due to osteoporosis or as a result of accident, by the device for noninvasive induction of dynamic deformation of body tissue.

Figure 4A:
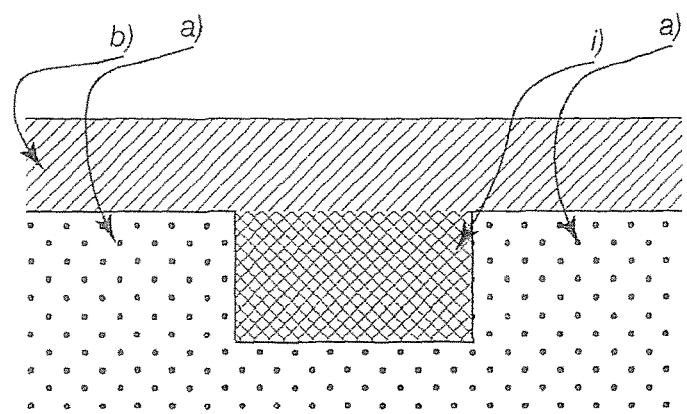
Figure 4B:
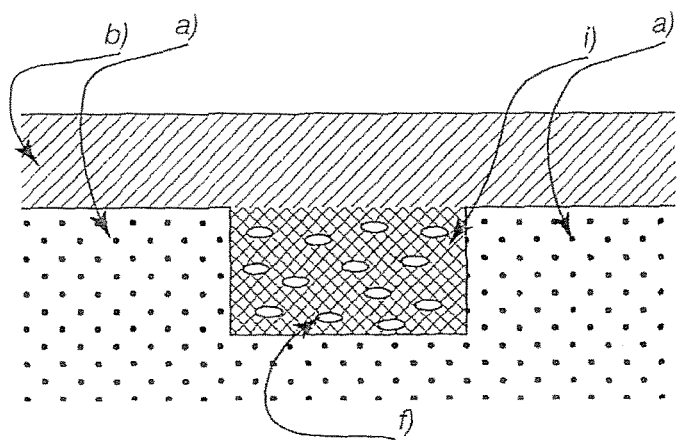

FIGS. 4a/b: The solution of suspended particles which can contain body cells is introduced at the location of the bone defect. This can be performed, for example, by injection.

Figure 4C:
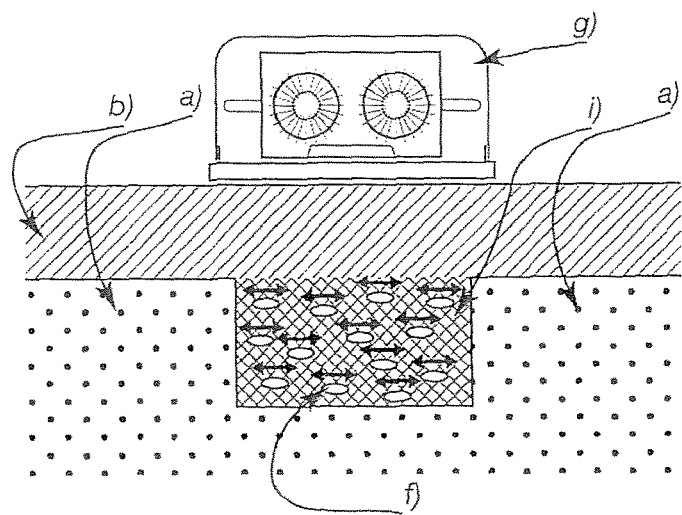

FIG. 4c: The actuator is externally attached. Upon its activation, mutual movements and thus strain, which are transmitted to the body cells and/or the body tissue, result in the solution of suspended particles which can contain the body cells. The body cells and/or the body tissue begin to differentiate.

Figure 4D:
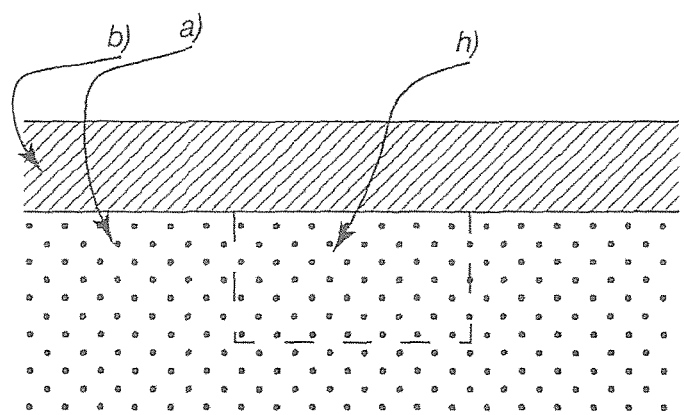

FIG. 4d: The bone is restored.

An example of other embodiment types of the particles which can be applied in combination with the above-mentioned examples.

Figure 5A:
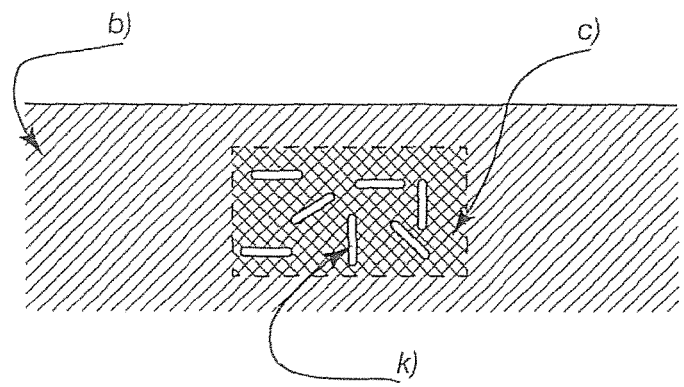

FIG. 5a: The solution of suspended particles which contain body cells is introduced. This can be performed, for example, by injection. The particles are formed as rods here.

Figure 5B:
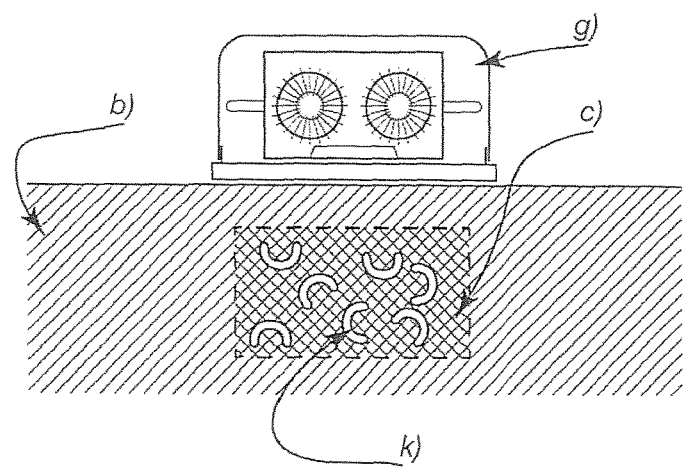

FIG. 5b: The actuator is externally attached. The rods deform upon its activation. A movement and thus a strain, which are transmitted to the body cells and/or the body tissue, thus result in the solution of suspended particles.

Figure 5C:
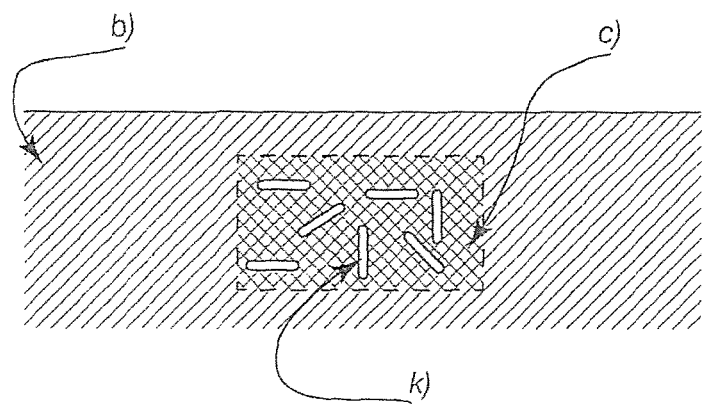

FIG. 5c: The actuator can also control the particles so that they merge back into the base position. The entire procedure can be repeated so that it is repeated in a frequency range and intensity which are optimum for the body cells and/or the body tissue, so that the optimum/desired differentiation is achieved.

Figure 5D:
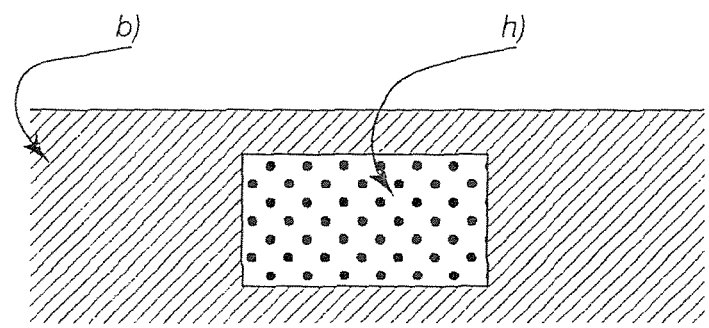

FIG. 5d: The body cells and/or the body tissue begin to differentiate. The particles can be resorbed by the body or are incorporated into the resulting body tissue. The advantage of the device for the induction of dynamic deformation of body tissue is, firstly, that the differentiation can be fundamentally initiated and, secondly, that the differentiation can be controlled in speed and resulting tissue.

EXAMPLE 1

Pseudoarthrosis Treatment

The patient suffers from a nonhealing bone fracture of the middle femoral bone after a traffic accident. The fracture consists of many parts. After a series of unsuccessful surgical osteosyntheses, the bone parts remain separate. The bone has partially broken down. One reason for the lack of healing is the absence of stimulation due to insufficient strain stimulus, caused by the geometrical complexity of the fracture. The traditional fixation of the bone parts does not permit a stimulation for the various bone intermediate spaces.

In this case, the stable traditional connection is left in the patient. A ringer solution admixed with magnetized or magnetically active neodymium particles having endogenous stem cells is injected into the nonhealing bone intermediate spaces.

The neodymium particles are enclosed by a plastic, so that they are body-compatible. The surface of the particles is formed in such a way that the movement is transferred in accordance with the purpose. The average volume of the neodymium particles used was 1,000,000 $\mu m^3$.

An array of further experiments was carried out using neodymium particles which had an average volume in the range of 1250-4,250,000 $\mu m^3$.

The injected ringer solution contained 50,000 particles per $mm^3$. An array of further experiments was carried out with endogenous liquid (instead of the ringer solution), having a particle density in the range of 250-200,000 units per $mm^3$.

The volume of the injected liquid corresponded to the intermediate space which had resulted in the existing bone fracture, in the specific case 5 cl.

After completed injection of the solution having the particles, an actuator for these particles was externally attached. It consisted of a fastening component and a technical component. The fastening component was designed as a sleeve made of textile material. The technical component consisted of a control module, an induction module, and a battery. The induction module consisted of two movable coils which were moved forward and backward upon the activation.

The actuator was set to a frequency of 6 inductions per hour ($\frac{1}{600}$ $sec^1$ (Hz)) and activated.

The healing was monitored by radiology, wherein the frequency and amplitude were adapted to the healing progress. The dimension of the amplitude was determined in that the tissue strain transferred by the particles resulted in the dimension of 100-2%.

The amplitude was reduced during the healing progress.

After 5 weeks, the healing was completed, the bones were solidly connected and loadbearing. The biochemically inert particles remained in the body until the excretion or were incorporated into the bone. The actuator was removed after completed healing.

EXAMPLE 2

Endogenous Bone Production

The patient suffered from a bone defect after a trauma as a result of a sports accident. Spongiosa was required as replacement bone. Obtaining the spongiosa represented a significant additional surgical intervention, which caused strong pains for a long time. In this case, the bone defect was filled with bony material by the invention in that a stem cell solution (MSC) enriched with thermally activatable particles was injected into the bone defect by injection.

The thermally activated particles were constructed so that a tension built up in the particles due to an externally introduced temperature change, which discharged upon reaching a limiting tension and a pulsed movement of the particles was generated. After the relaxation and the reaching of the body temperature, the particles were ready again for a further cycle. The particles used were of oblong shape and were constructed from multiple layers of various thermally reacting metals (in a further experiment, a memory alloy was used for this purpose). The particles were externally coated using an elastic, body-compatible plastic protective layer. The surface was formed so that the movement was transferred appropriately.

The average size of the particles was 0.1 mm.

The number of particles per unit of volume of the injected solution was 10 units per $mm^3$.

The thermal actuator used in this experiment consisted of a fastening component and a technical component. The fastening component was embodied as a textile sleeve.

The technical component consisted of a control module, an induction module, and a battery. The induction module was a heat source, which was based on thermal induction and heated the particles in the solution in the bone defect located close to the surface so that they could carry out the provided movement without damaging the surrounding tissue.

Is externally attached. The frequency set at the actuator was 2 times per hour, i.e., was set to $\frac{1}{1800}$ $sec^{-1}$ (Hz).

The power of the actuator was set so that the particles were activated appropriately without damaging the surrounding tissue. The particles were heated enough that the movement was not damaging to tissue.

The particles exerted a strain on the MSC contained in the solution due to the thermal activation. They began to differentiate and formed endogenous spongiosa bone in a pain-free manner within approximately 6 weeks.

Upon the activation of the particles, their volume remained constant, only their shape changed from curved to linear, as shown in FIGS. 5a, b, and c.

EXAMPLE 3

Bone Lengthening

The patient suffered since adolescence from a one-sided shortening of the lower leg of 20 mm due to a growth defect.

To counteract foreseeable postural defects, the length of the affected limb was supposed to be adapted. For this purpose, the two lower leg bones of the shortened leg were severed at a suitable point in a surgical invention and stabilized by means of traditional orthopedic fixing methods so that both legs were of equal length. A segment resulted in which the bone was absent. A solution having particles which had a large specific mass was injected into this segment. The particles consisted of a core of high specific mass and a biocompatible jacket. The surface was formed so that the movement was transferred appropriately by adhesion of the tissue. The core of the particles consisted of platinum, the jacket of etched titanium. The mean size of the particles was 0.15 mm. The number of the particles per unit of volume of the injected solution was 8 units per $mm^3$.

The quantity of injected solution was 6 ml.

The actuator adapted to this particle was externally attached to the leg and activated 3 times per hour. (1/1200 Hz).

The actuator functioned according to the principle of resonance and consisted of a fastening component and a technical component. The fastening component was a sleeve made of plastic in this application. The technical component consisted of a control module, an induction module, and a battery. The induction module was a movement source which was based on rotation imbalance and which moved the particles in the solution in the bone defect in relation to the surrounding tissue because of their mass inertia.

The healing was radiologically monitored. The frequency and amplitude were adapted to the healing progress.

The tissue cells, on which a strain stimulus acted, began to differentiate, beginning with a cell-containing liquid. This converted approximately in cycles of a week in granulation tissue, into resilient connective tissue.

After 6 weeks, the healing was completed, the bones were solidly connected and loadbearing. The biochemically inert particles remained in the body until excretion or were incorporated into the bone. The actuator was removed after completed healing.

EXAMPLE 4

Tissue Engineering

The patient suffered from a sports-related dysfunction in the left shoulder joint, which was painful. A new joint capsule was supposed to be produced for this purpose. It was produced from a connective tissue membrane. The connective tissue membrane was produced in the body using the method according to the invention.

For this purpose, a flat pocket was produced subcutaneously by surgery in the abdomen region. A solution having particles which had a large specific mass was injected into this pocket. The particles consisted of a core of high specific mass and a biocompatible jacket. The surface was formed so that the movement was transferred appropriately by adhesion of the tissue. The core of the particles consisted of platinum, the jacket of etched titanium.

For this application, the particles had a mean length of 0.2 mm.

The number of the particles per unit of volume of the injected solution was 7 units per $mm^3$.

The quantity of injected solution was 8 ml.

The actuator adapted to these particles functioned according to the principle of resonance and consisted of a fastening component and a technical component. The fastening component was a sleeve made of plastic in this application. The technical component consisted of a control module, an induction module, and a battery. The induction module was a movement source which was based on rotation imbalance and which moved the particle in the solution in the bone defect in relation to the surrounding tissue because of their mass inertia.

The actuator was externally attached to the abdomen and activated 3 times per hour. (1/1200 Hz).

The healing was radiologically monitored. The frequency and amplitude were adapted to the healing progress. After 3 weeks, the connective tissue membrane had formed in the subcutaneous pocket. This tissue was removed in a surgical intervention and was used to replace the defective tissue capsule. The biochemically inert particles remained in the body until excretion or were incorporated into the bone. The actuator was removed after completed healing.

Although various embodiments of the present invention exist as described above, these are to be understood so that the various features can be used both individually and also in any arbitrary combination.

This invention is therefore not simply restricted to the above-mentioned, particularly preferred embodiments.

The invention claimed is:

1. A device for noninvasive induction of dynamic deformation of body tissue to differentiate tissue cells, which comprises the following components:
   (i) a suspension of particles suspended in a solution; and
   (ii) an external actuator;
   wherein:
   a) the particles are metallic, magnetic, magnetizable, electrically chargeable, or thermally reactive;
   b) the average diameter of the particles is greater than 5 µm and less than 5 mm;
   c) the external actuator comprises a vibration source or a heat source or is configured to emit electromagnetic waves or to generate an electrical field to stimulate the suspended particles vibrationally, thermally, magnetically or electrically;
   d) the solution is a body-compatible liquid that contains bone-forming substances and/or tissue components and/or stem cells;
   e) the suspended particles are structurally configured so as to be capable of being repeatedly stimulated by the external actuator, after injection into the body tissue, to move and thereby noninvasively induce dynamic deformation of the body tissue to differentiate the tissue cells; and
   f) wherein the particles comprise one or more substances selected from the group consisting of platinum, titanium, steel, carbon steel, martensitic steels, crystalline and amorphous alloys based on iron, nickel, cobalt, soft ferrites, hard ferrites, cobalt samarium, neodymium iron-boron, AlNiCo and memory alloys.

2. The device as claimed in claim 1, wherein the suspension further comprises body cells.

3. The device as claimed in claim 1, wherein the particles are nonporous.

4. The device as claimed in claim 1, wherein the particles comprise electrically conductive materials which have a rest potential different from surroundings due to an insulating outer skin.

5. The device as claimed in claim 1, wherein the particles comprise a bioresorbable material.

6. The device as claimed in claim 1, wherein the particles are homogenous to each other at least in their respective cores.

7. The device as claimed in claim 2, wherein the particles are provided with a biocompatible outer skin, which is capable of promoting growth of the body cells.

8. The device as claimed in claim 1, wherein the average diameter of the particles is less than 50 μm.

9. The device as claimed in claim 1, wherein the average volume of the particles on an individual basis is greater than 125 μm$^3$.

10. The device as claimed in claim 1, wherein the average volume of the particles on an individual basis is less than 100 mm$^3$.

11. The device as claimed in claim 1, wherein the particles do not have a fibrous structure.

12. The device as claimed in claim 1, wherein at most $10^6$ particles are contained per mm$^3$ of the body-compatible liquid.

13. The device as claimed in claim 1, wherein the ratio between the volume of the particles in the suspension and the volume of the solution in the suspension is at most 10:1.

14. The device as claimed in claim 1, wherein the ratio between the volume of the particles in the suspension and the volume of the solution in the suspension is at least 1:1000.

* * * * *